(12) United States Patent
Richter et al.

(10) Patent No.: US 9,289,170 B2
(45) Date of Patent: Mar. 22, 2016

(54) APPARATUS FOR ELICITING A BLOOD SAMPLE

(71) Applicant: SANOFI-AVENTIS DEUTSCHLAND GMBH, Frankfurt am Main (DE)

(72) Inventors: Frank Richter, Frankfurt am Main (DE); Ross MacArthur, Cheshire (GB)

(73) Assignee: SANOFI-AVENTIS DEUTSCHLAND GMBH, Frankfurt Am Main (DE)

( * ) Notice: Subject to any disclaimer, the term of this patent is extended or adjusted under 35 U.S.C. 154(b) by 116 days.

(21) Appl. No.: 14/359,351

(22) PCT Filed: Nov. 21, 2012

(86) PCT No.: PCT/EP2012/073254
§ 371 (c)(1),
(2) Date: May 20, 2014

(87) PCT Pub. No.: WO2013/076152
PCT Pub. Date: May 30, 2013

(65) Prior Publication Data
US 2014/0330165 A1  Nov. 6, 2014

(30) Foreign Application Priority Data

Nov. 25, 2011 (EP) .................................. 11190679

(51) Int. Cl.
*A61B 5/00* (2006.01)
*A61B 5/151* (2006.01)
*A61B 5/15* (2006.01)

(52) U.S. Cl.
CPC ........... *A61B 5/15101* (2013.01); *A61B 5/1411* (2013.01); *A61B 5/150022* (2013.01); *A61B 5/15113* (2013.01); *A61B 5/150412* (2013.01); *A61B 5/150511* (2013.01); *A61B 5/150534* (2013.01); *A61B 5/150702* (2013.01)

(58) Field of Classification Search
CPC .................................................... A61B 5/15101
USPC ........................... 600/583, 584; 606/181–183
See application file for complete search history.

(56) References Cited

U.S. PATENT DOCUMENTS

2003/0109777 A1   6/2003   Kloepfer et al.

FOREIGN PATENT DOCUMENTS

| DE | 102009002019 | 10/2010 |
|---|---|---|
| GB | 2331936 | 6/1999 |
| WO | 2004/098410 | 11/2004 |
| WO | 2012/004354 | 1/2012 |

OTHER PUBLICATIONS

International Search Report for Int. App. No. PCT/EP2012/073254, completed Dec. 10, 2012.

*Primary Examiner* — Brian Szmal
(74) *Attorney, Agent, or Firm* — McDonnell Boehnen Hulbert & Berghoff LLP (57) ABSTRACT

An apparatus for eliciting a blood sample is presented having a lancet for lancing a body part of a user and a cleaning member of absorbent material operable to clean a surface of the body part, the apparatus being configured such that in use the lancet is moved to lance a body part of a user and subsequently the cleaning member is moved to contact the body part of the user so as to remove blood from the surface of the body part prior to collection of the blood sample from the surface of the body part.

15 Claims, 10 Drawing Sheets

Fig. 11

# APPARATUS FOR ELICITING A BLOOD SAMPLE

CROSS REFERENCE TO RELATED APPLICATIONS

The present application is a U.S. National Phase Application pursuant to 35 U.S.C. §371 of International Application No. PCT/EP2012/073254 filed Nov. 21, 2012, which claims priority to European Patent Application No. 11190679.8 filed Nov. 25, 2011. The entire disclosure contents of these applications are herewith incorporated by reference into the present application.

TECHNICAL FIELD

This invention relates to apparatus for eliciting a blood sample.

BACKGROUND

Diabetes sufferers may be provided with quantities of insulin, for instance by injection, sometimes a number of times daily. The quantity of insulin that is appropriate depends on the person's blood glucose level, so blood glucose level measurement can also occur a number of times daily.

Blood glucose level measurement typically is a multi stage process. The first is lancing, in which a lancet, or needle, is used to pierce the skin of a user, for example on the end or side of a finger. Once a suitable amount of blood has been produced, a sample is taken on a testing strip. A person may need to squeeze their finger in order to cause sufficient blood to be expelled. Sometimes lancing needs to be reperformed. The testing strip then is provided to a meter, typically an electronic meter, which analyses the sample, for example by determining a parameter (e.g. an electrochemical potential or voltage, resulting from a chemical reaction between the blood sample and an enzyme present in the testing strip, and provides a blood glucose measurement result. This measurement is then used to determine an amount of insulin to be consumed by the person.

SUMMARY

A first aspect of the invention provides an apparatus for eliciting a blood sample, the apparatus comprising:
  a lancet for lancing a body part of a user; and
  a cleaning member of absorbent material operable to clean a surface of the body part, the apparatus being configured such that in use the lancet is moved to lance a body part of a user and subsequently the cleaning member is moved to contact the body part of the user so as to remove blood from the surface of the body part prior to collection of the blood sample from the surface of the body part.

The cleaning member may be further configured to contact the body part of the user prior to lancing so as to clean the surface of the body part. The cleaning member may contain an antiseptic. The lancet may be flexible and resilient.

The apparatus may be a disc-like member and the lancet and the cleaning member may be supported by a housing disposed at an edge of the disc-like member.

The apparatus may be a testing member and may further comprise a blood analysis part for receiving the blood sample.

The apparatus may be configured to be rotatably mounted on a shaft and to be rotated between a first rotational position and a second rotational position in order to perform the lancing of the body part. The cleaning member may be configured to contact the user's body part to remove blood from the surface thereof during rotation between the second rotational position and the first rotational position.

The apparatus may further comprise:
  a camera configured to capture images of the user's body part; and
  a processor configured to:
    control operation of the camera;
    receive the captured images; and
    determine whether blood is present on the surface of the user's body part.

The apparatus may further comprise a seal arranged to cover the lancet and the cleaning member.

The whole of the lancet may be arranged to be retained within a boundary defined by the seal in a first configuration and a cutting end of the lancet may be arranged to protrude beyond a boundary defined by the seal in a second configuration.

A second aspect of the invention provides a device comprising:
  a housing;
  a shaft supported within the housing; and
  a plurality of apparatuses each according to the first aspect of the invention, wherein each apparatus may be rotatably mounted on the shaft and may be moveable along the shaft.

The seal of each apparatus may be configured to be removed by rotational movement of that apparatus within the housing. The seal of each apparatus may be configured to be removed by movement of that apparatus along the shaft.

A third aspect of the invention provides a method of operating a lancing device comprising means for receiving a body part of a user and a rotatable testing member having a lancet and a cleaning member, the method comprising:
  rotating the testing member in a first direction such that the cleaning member contacts a body part of a user received in the receiving means;
  rotating the testing member further in the first direction such that the body part of the user is lanced by the lancet; and
  rotating the testing member in a second direction such that the cleaning member contacts the body part of the user so as to remove blood from the surface of the body part.

BRIEF DESCRIPTION OF THE DRAWINGS

Embodiments of the invention will now be described, by way of example only, with reference to the accompanying drawings, in which.

DETAILED DESCRIPTION

Figure 1:
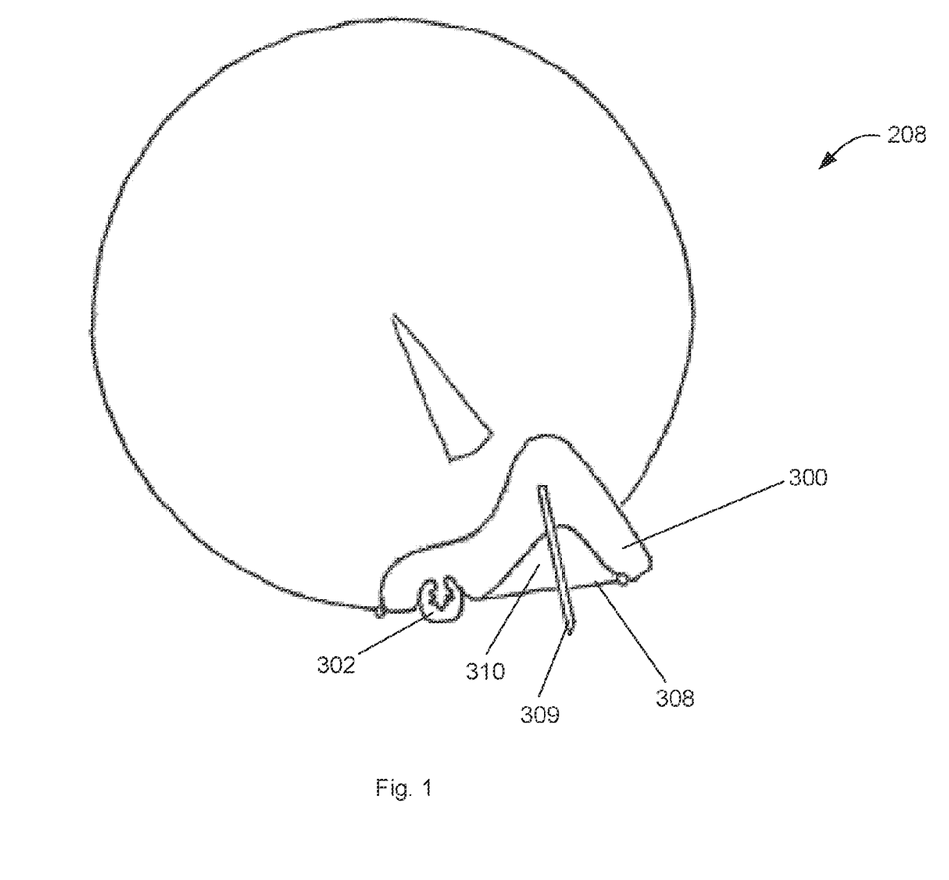
FIG. 1 is a cross-sectional plan view of a lancing device according to aspects of the invention.
Figure 2:
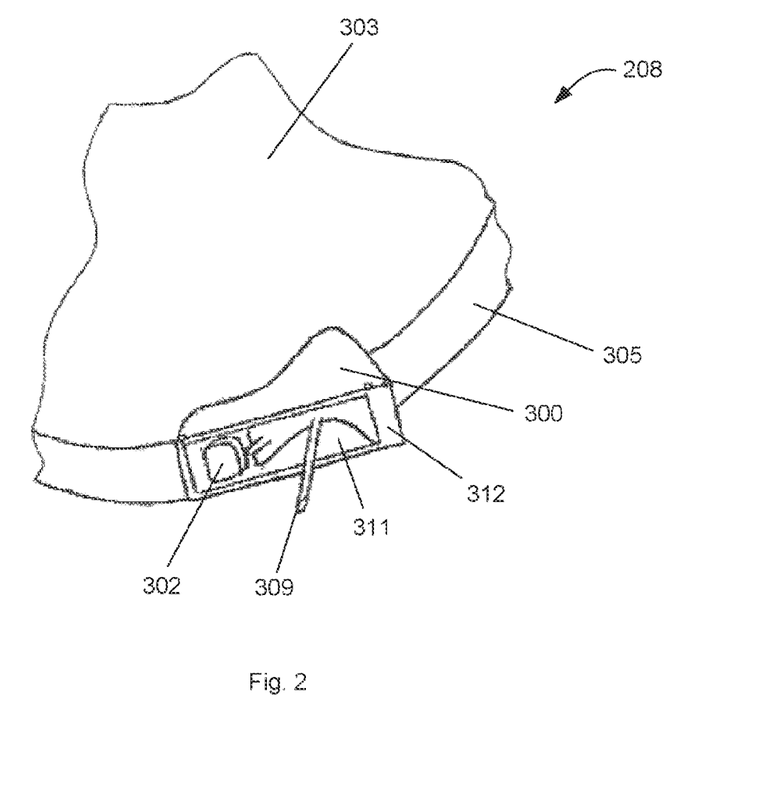
FIG. 2 is a perspective view of a portion of the lancing device of FIG. 1.

Referring to FIGS. 1 and 2, a lancing device 208 is shown. Only a portion of the lancing device 208 is shown in FIG. 2. The lancing device 208 has a generally disc like shape. The lancing device 208 includes an uppermost surface 303, a lowermost surface (not visible) and an edge 305. In some embodiments, the diameter of the lancing device 208 is between 15 and 25 millimeters, for instance 20 millimeters. The thickness of the device 208, which is equal to the height of the edge 305, is between 0.5 millimeters and 3 millimeters.

A lancet housing 300 is provided at a point on the circumference of the lancing device 208. The lancet housing 300 may be an insert which communicates with a corresponding recess in the edge 305 of the lancing device 208. Alternatively the lancing device 208 may have a correspondingly shaped cut-away portion and the lancet housing 300 may be receiving in this portion. The lancet housing 300 may be secured within the recess or cut-away portion by an adhesive or by any other suitable means. Alternatively, or in addition, the lancet housing may be thicker than the edge 305 of the lancing device 208, and the top and bottom surfaces of the lancet housing 300 may each comprise protruding lips which provide frictional connections to the uppermost and lowermost surfaces of the lancing device 208 respectively. The lancet housing 300 may be made of a material with some flexibility and resilience in order to provide or enhance the frictional connection. The lancet housing 300 may, for example, be made of a plastic material.

The lancet housing 300 is substantially triangular in cross-section. However the shape of the lancet housing 300 is not limiting and it will occur to the skilled person that other geometric or irregular cross-sections may be used. The lancet housing 300 is angled relative to a radial line of the lancing device 208 such that one corner of the lancet housing 300 is flush with the edge 305 of the lancing device 208 and another corner of the lancet housing 300 protrudes from the edge 305. An outwardly facing edge 308 connects these two corners. Alternatively, the lancet housing 300 may be shaped or angled such that the outwardly facing edge 308 of the lancet housing 300 is flush or substantially flush with the edge 305 of the lancing device 208.

A lancet 309 is shown protruding from the lancet housing 300. A first end of the lancet 309 is embedded within the material of the lancet housing 300, and a second end is provided with a sharp point and extends outwardly. The lancet 309 extends at an angle between 30 and 90 degrees from a radius line of the lancing device 208 at the position where the end of the lancet 309 is embedded in the lancet housing 300. The second end of the lancet 309 protrudes beyond the outwardly facing edge 308 of the lancet housing 300 in the configuration shown in FIGS. 1 and 2. The lancet 309 may, for example, be made of a metal material.

An aperture 311 is provided in the outwardly facing edge 308 of the lancet housing 300. A space 310 is provided within the body of the lancet housing 300, the space 310 being open to the outside via the aperture 311. The aperture 308 may comprise substantially the whole of the outwardly facing edge 308, leaving only thin rails 312 at the edges of the outwardly facing edge 308.

Figure 3:
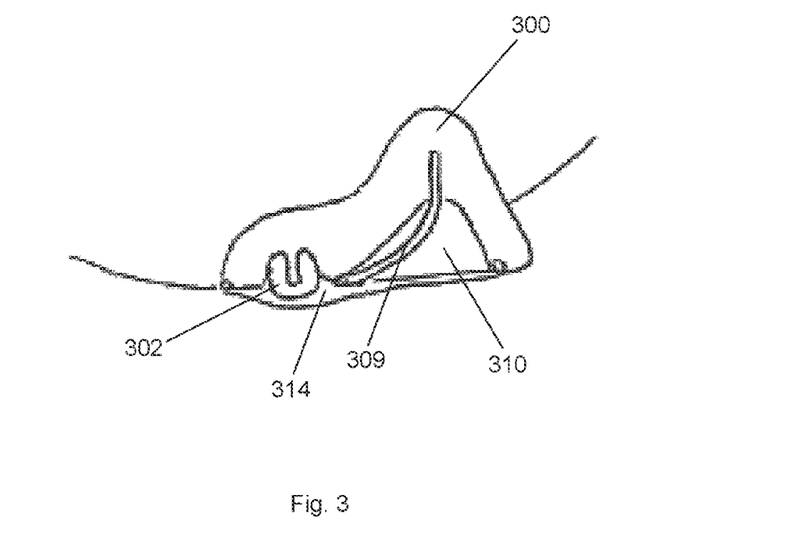
FIG. 3 is a cross-sectional plan view of a portion of the lancing device of FIG. 1 showing the position of the lancet when a seal is in place.

The lancet housing 300 also supports a cleaning swab 302. The cleaning swab 302 may be referred to as a cleaning member and is an absorbent member comprising an absorbent material. The cleaning swab 302 may be impregnated with an antiseptic solution throughout the body of the cleaning swab 302. This may be an alcohol solution. A recess may be provided in the lancet housing 300 to receive the cleaning swab 302. The cleaning swab 302 may be secured in the recess by frictional connection and/or by an adhesive. The cleaning swab 302 may be a foamed material such as a sponge. In some embodiments, the cleaning swab 302 is not saturated with liquid such that it is capable of absorbing more liquid. The cleaning swab 302 is shown in FIGS. 1 to 3 as being supported on a separate part of the lancet housing 300 from the space 310. However, in some other embodiments, the cleaning swab 302 may be supported within the space 310. The cleaning swab 302 is arranged so as to protrude from the outwardly facing edge 308 of the lancet housing 300.

In some alternative embodiments, the lancet housing 300 may be omitted and the lancet 309 and cleaning swab 302 may be disposed directed on the edge 305 of the lancing device 208.

FIGS. 1 and 2 represent the lancing device 208 in an operational arrangement. Referring now to FIG. 3, the lancing device 208 is shown in a storage or pre-operational arrangement. In this arrangement, the outwardly facing edge 308 of the lancet housing 300 is covered by a seal 314. The seal 314 may be attached to the outwardly facing edge 308 of the lancet housing 300 along the rails 312 by a weak adhesive. The seal 314 may alternatively be secured by a heat seal connection. The seal 314 may have extensions along one or more of its edges which are not secured to the rails 312 and which provide one means of removing the seal 314.

The lancet 309 may be made of a resilient material, for example a flexible metal material. This allows the lancet 309 to be bent when a bending force is applied to it and to return to its original shape when the force is removed. In the pre-operational arrangement of FIG. 3, the seal 314 is providing the force to keep the lancet 309 in the bent configuration. The lancet 309 must be flexible enough so that it can easily be bent and retained in a bent configuration by action of the seal 314, but also rigid enough that it does not buckle when used to lance a body part of a user. In some embodiments, parts of the lancet 309 may be made of a rigid material and other parts may be made of a flexible material. For example, a portion of the piercing end of the lancet 309 and the portion of the lancet 309 which is embedded in the lancet housing 300 may be made of a rigid material. A central portion of the lancet may be made of a more flexible material.

The seal 314 ensures that the lancet 309 and cleaning swab 302 remain sterile before use. The seal 314 may be a hermetic seal. The seal 314 also prevents the alcohol absorbed within the cleaning swab 302 from evaporating. In some embodiments, the seal 314 also separates the cleaning swab 302 from the space 310 which houses the lancet 309. This further assists in preventing evaporation of the alcohol.

In use, one or more of the lancing devices 208 may be rotatably mounted in a housing. The lancing device 208 may be moved into an operational position within the housing when the seal 314 is removed, releasing the lancet 309 and uncovering the cleaning swab 302. A user may then present a body part to be lanced, for example a digit, against an aperture or within a recess in the housing and the lancing device 208 may be rotated. In the illustrated embodiments, the lancet 309 is angled in a clockwise direction and the cleaning swab 302 is located clockwise of the lancet. Therefore, the lancing device 208 rotates from an initial position in a clockwise direction so that the user's digit is first contacted by the cleaning swab 302. The user's digit is then lanced by the lancet 309. The extent of the rotation of the lancing device 208 may be preset such that the depth of the lancing is also preset. After lancing, the lancing device 208 then rotates in an anti-clockwise direction such that the cleaning swab 302 again contacts the user's digit and removes the blood from the surface of the user's digit. The user then removes their digit in order to provide a blood sample from the lancet wound for analysis at an external meter. Exemplary operation of the lancing device 208 is described in greater detail with respect to the flow chart of FIG. 11.

Figure 4:
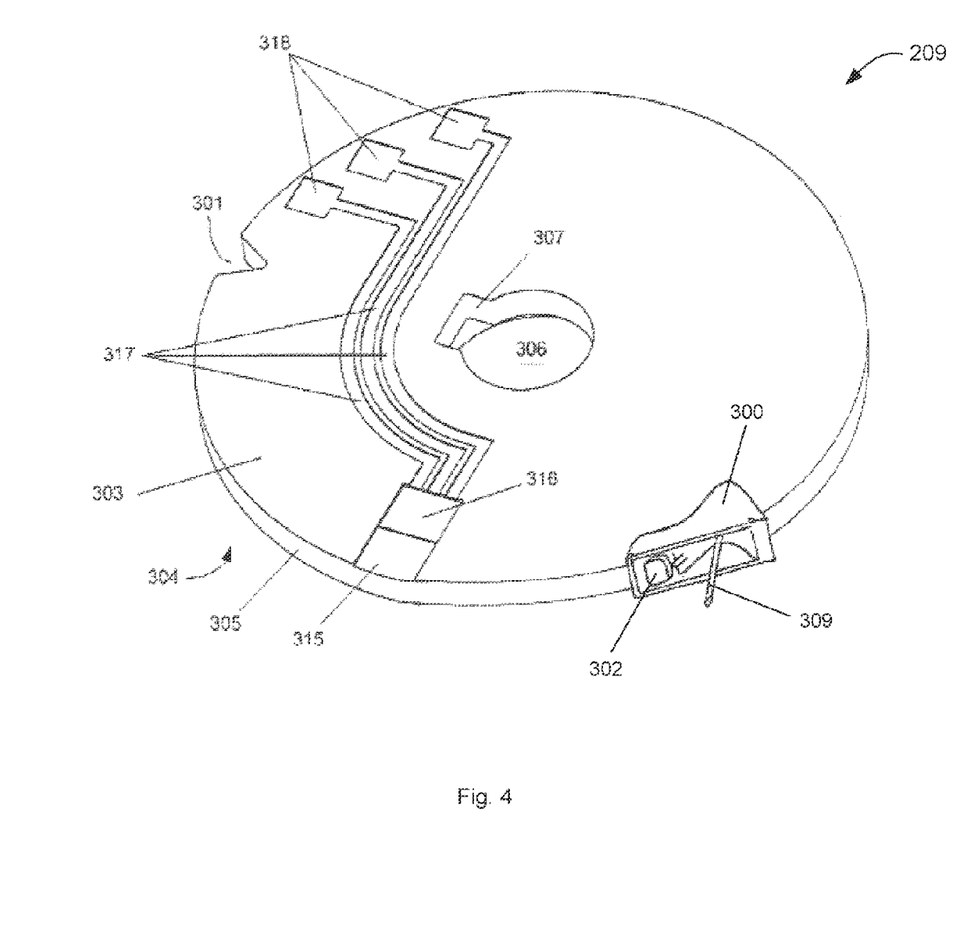
FIG. 4 is a perspective view of a second embodiment of a lancing device.

A second embodiment of a lancing device is shown in FIG. 4. This lancing device may also be referred to as a test disc member 209. The test disc member 209 is similar in shape and construction to the lancing device 208 of the first embodiment described above. The test disc member 209 includes an uppermost surface 303, a lowermost surface (not visible) and a disc edge 305. The diameter of the test disc member 209 is between 15 and 25 millimeters, for instance 20 millimeters. The thickness of the disc, which is equal to the height of the disc edge 305, is between 0.5 millimeters and 3 millimeter.

As well as comprising the lancet housing 300, with lancet 309 and cleaning swab 302, a hole 306 is formed at the center of the test disc member 209. The hole 306 comprises two main parts. A circular part is centered on the test disc member 209. A drive notch 307 abuts the circular part of the hole 306. The hole 306 allows the test disc member 209 to be mounted on a shaft. The drive notch 307 allows the test disc member 209 to be engaged by driving means and to be rotated with the shaft. The hole 306 and drive notch 307 depicted in FIG. 4 may also be provided in the first embodiment of FIGS. 1 to 3 in order to allow the lancing device 208 to be mounted on a shaft and to be rotated as described above.

The test disc member 209 further comprises a blood collection part 315 located at the edge of the test disc member 209. This may take any suitable form. For instance, it may comprise a laminated material. The blood collection part 315 has the function of drawing blood that is in contact with it into the test disc member 209 to a blood analyte measuring part 316, that adjoins the blood collection part 315, for example a part containing an enzyme for blood glucose measuring, or the like. Blood may be drawn through capillary action. The analyte measuring part 316 includes an enzyme that reacts chemically with blood in such a way that blood glucose level can be measured. The analyte measuring part 316 is connected to first to third contact pads 318 by first to third conductive tracks 317. The contact pads 318 and the conductive tracks 317 are formed on the upper surface 303 of the test disc member 209. The blood collection part 315 and analyte measuring part 316 are also is formed on the upper surface 303 of the test disc member 209. Some or all of the conductive tracks 317, the contact pads 318 and the analyte measuring part 316 may be printed onto the upper surface 303 of the test disc member 209.

In this second embodiment, after the user's digit has been lanced and the first droplet of blood has been removed by the cleaning swab 302, the test disc member 209 is rotated further such that the user's digit contacts the blood collection part 315. This blood is absorbed into the analyte measuring part 316. A measuring circuit connected to the analyte measuring part 316 by way of the conductive tracks 317 and the contact pads 318 then is able to determine a blood glucose level of the blood. This level may then be displayed to the user.

Figure 5:
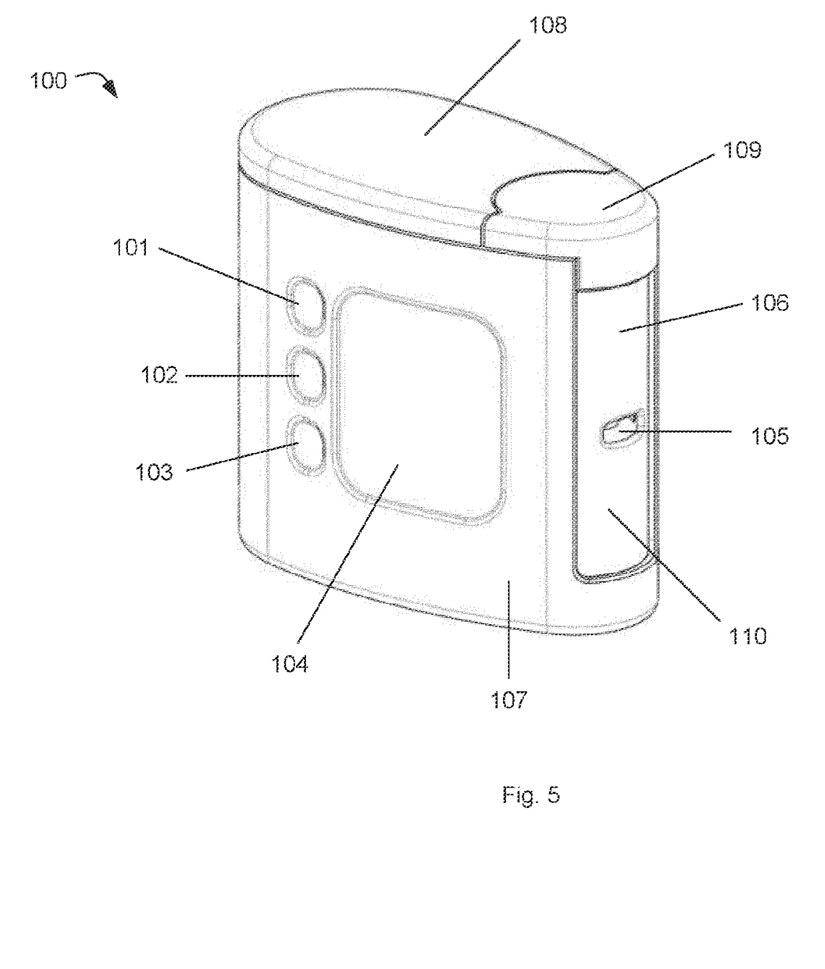
FIG. 5 is a perspective view of a blood glucose meter (BGM) suitable for use with the lancing devices of FIGS. 1 to 4.

The test disc member 209 may form part of an all in one blood glucose meter (BGM) 100. An exemplary BGM 100 is shown in FIG. 5. The BGM 100 is shown in a perspective view. The BGM 100 has a generally flat base that is not visible in the figure. The BGM 100 is approximately as tall as it is long, and its width is approximately one-third of its height On one side face of the BGM are provided first, second and third inputs 101, 102, 103. These may take the form of push-switches or touch sensitive transducers, for instance. Also provided on the side of the BGM next to the input devices 101 to 103 is a display 104. This may take any suitable form, for instance a liquid crystal display (LCD), e-ink etc. In use, a user may control the BGM 100 using the input devices 101 to 103 and may be provided with information by the BGM through the display 104.

Located at a front face of the BGM 100 is an aperture 105. The aperture 105 is located at approximately half of the height of the BGM. The aperture 105 is configured such as to be able to receive a part of a user's body, for the purpose of extracting a blood sample therefrom. For instance, the aperture 105 may be dimensioned so as to receive an end or a side part of a finger or thumb, or may be dimensioned so as to receive a side of a user's hand or a pinch of skin from a user's arm. The aperture may be rectangular in shape. Its edges may be bevelled, so as to guide a user's digit into a specific location.

The aperture 105 is provided in the side of a cartridge 106. The cartridge has a generally cylindrical form, and is arranged vertically in the BGM 100.

In particular, the BGM includes a first housing part 107. The first housing part 107 forms the base, left and right side face and the rear face of the BGM 100. On the front face of the BGM 100, the first housing part 107 also comprises the lowermost part of the side face. A fixed lid part 108 is attached to the first housing part 107. The fixed lid part 108 comprises most of the top surface of the BGM 100. A removable lid part 109 comprises the remaining part of the top surface of the BGM 100. The removable lid part is disposed above the cartridge 106 at the front face of the BGM 100.

The first housing part 107 is configured such as to provide an elongate aperture 110 at the front face of the BGM 100. The elongate aperture 110 may extend for most of the height of the front face of the BGM 100. The elongate aperture 110 is defined at the uppermost part by the removable lid part 109 and is defined by the first housing part 107 at the right, left and bottom. The BGM 100 is arranged such that the cartridge 106 occupies the whole of the area of the elongate aperture 110. A slidable or pivotable door in the housing part 107 of the BGM 100 may cover all or a part of the elongate aperture 110 when the BGM is not in use. The door may cover at least the aperture 105, such as to prevent the ingress of dirt and other potential contaminants into the aperture 105.

Figure 6:
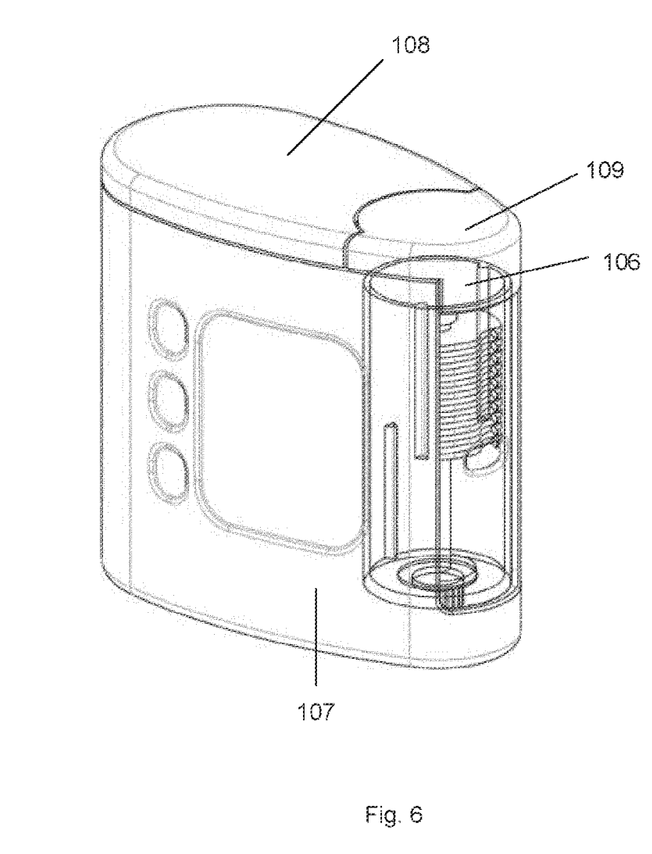
FIG. 6 is a perspective view of the BGM of FIG. 5 with a portion shown as transparent, so as to allow features inside a housing to be seen.

The cartridge 106 is more clearly visible in FIG. 6. FIG. 6 shows the same view as FIG. 5, although the removable lid part 109 and the first housing part 107 are shown in wire frame. As can be seen from FIG. 6, the cartridge 106 has a generally cylindrical form, and is arranged vertically. The diameter of the cartridge 106 is greater than the width of the aperture 110 by a factor for instance of between 5 and 50%. The cartridge 106 has a length that is between 3 or 4 times its diameter.

Figure 7:
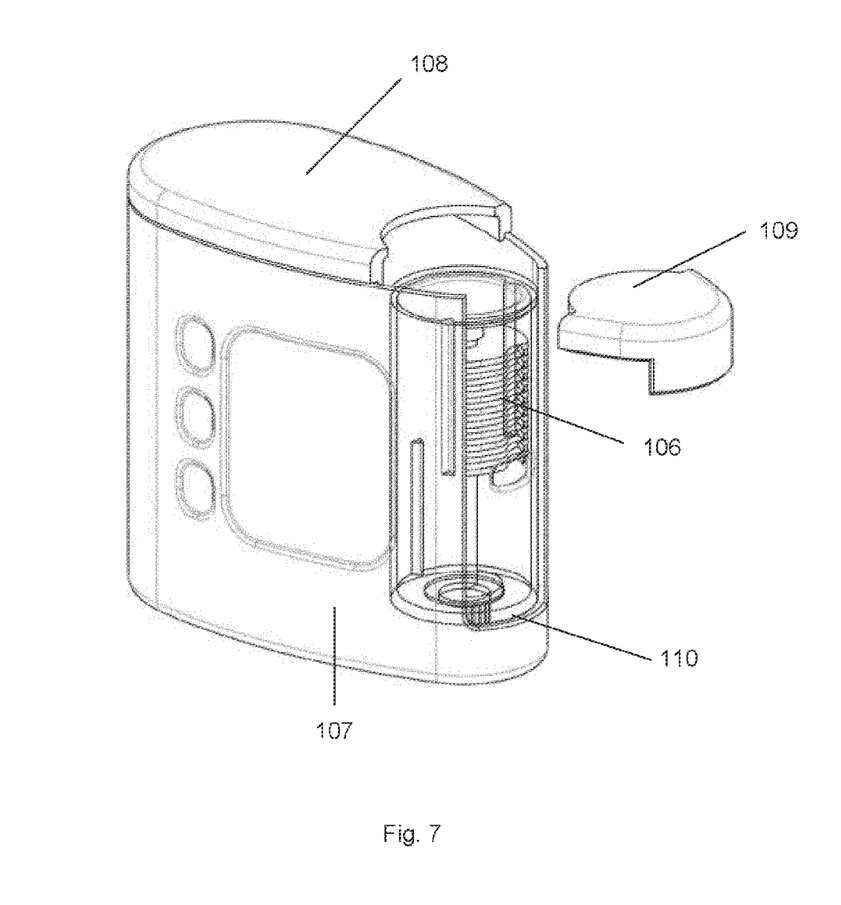
FIG. 7 is the same as FIG. 6 although a lid portion is shown as being removed.

In FIG. 7, the removable lid part 109 is shown as having been removed from the BGM 100. The first housing part 107, the fixed lid part 108 and the removable lid part 109 are configured such that when the removable lid part is in place on the BGM the cartridge 106 is retained by mechanical interaction between the three components but is removable by a user. The exact way in which the removable lid part 109 is released from the BGM 100 is not critical and is not described in detail here.

Figure 8:
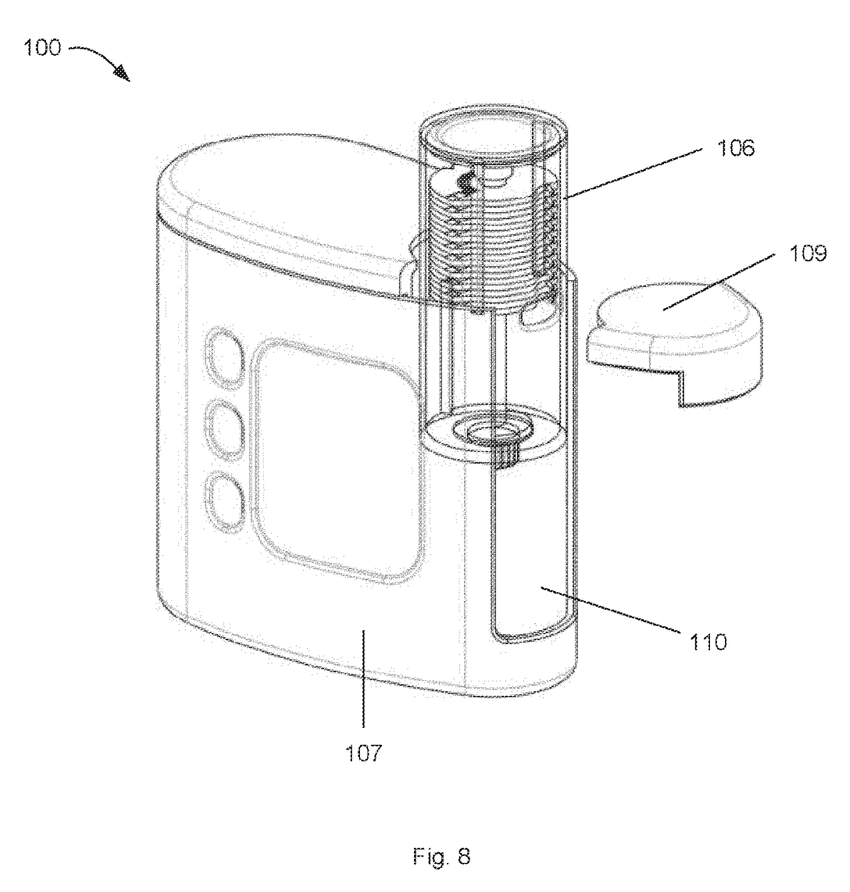
FIG. 8 is the same as FIG. 7, although a cartridge is shown as partly removed.

The removable lid part 109 is configured such that when removed from the BGM 100 the cartridge 106 is able to be extracted from the BGM by moving it vertically along its axis. In FIG. 8, the cartridge 106 is shown as being partly removed from the BGM 100. When fully removed, the elongate aperture 110 reveals a cavity in the BGM 100. A replacement cartridge can then be introduced into the BGM 100 in the opposite manner to which the old cartridge 106 was removed. Once located at the bottom of the cavity in the BGM, the new cartridge 106 is partly surrounded by the first housing part 107. Once the removable lid part 109 has been replaced, to the position shown in FIG. 5, the cartridge 106 is retained in place by the action of the first housing part 107 and the removable lid part 109. The aperture 105 in the cartridge 106 is presented at the front face of the BGM 100, in the same way as shown in FIG. 5. The cartridge 106 and the cavity which receives the cartridge may have a keying feature, such as a protrusion and a groove, a non circular diameter, or the like. Thus, when the cartridge 106 is fully inserted, the aperture 105 is in a fixed position to the elongate aperture 110, for example in a centered position as shown in FIG. 5.

As can be seen in FIGS. 6 to 8, the cartridge 106 contains a plurality of test disc members 209 in a stack. The BGM may be configured to present each of the test disc members 209 to the aperture 105 in turn.

Figure 9:
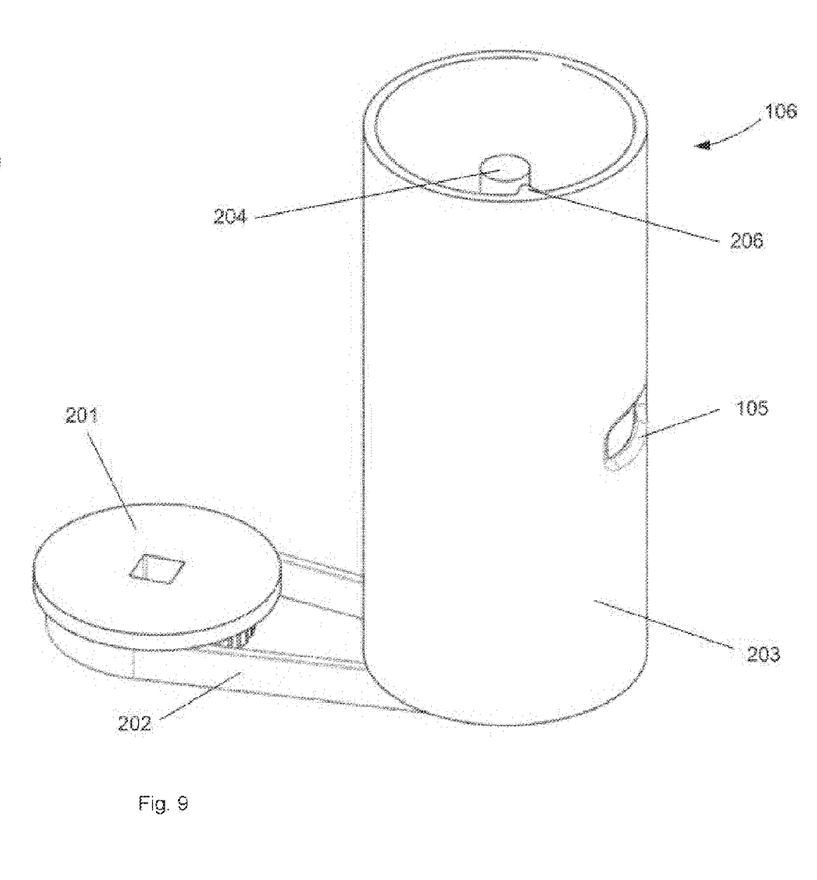
FIG. 9 illustrates components of one embodiment the BGM of FIG. 5.

FIG. 9 shows a subsystem 200 of the blood glucose meter 100. The subsystem 200 includes the cartridge 106, a drive wheel 201 and a drive belt 202.

In FIG. 9, the cartridge shown as having a hollow cylindrical housing part 203, which constitutes part of a housing. The aperture 105 is formed in the hollow cylindrical housing part 203. Coaxial with the hollow cylindrical part 203 is an elongate shaft 204, only the top part of which is illustrated in FIG. 9. The length of the shaft 204 is such that its uppermost end is slightly below the uppermost end of the hollow cylindrical housing part 203. As will be described below, the shaft 204 is mechanically coupled with the drive belt 202 so as to be rotatable by rotation of the drive wheel 201.

Formed with the inner surface of the hollow cylindrical housing part 203 is a first guide member 206. In FIG. 9, it can be seen that the first guide member 206 has a generally triangular cross section. One side of the triangular cross section is integral with the inner surface of the hollow cylindrical housing part 203, with a point of the triangular cross section extending towards the center of the cartridge 106. only the uppermost surface of the first guide member 206 is visible in FIG. 9.

The first guide member 206 is located only in the uppermost half of the length of the cartridge 106. A second guide member (not visible) is located in the lowermost half of the cartridge 106. The first and second guide members are distributed around the circumference of the hollow cylindrical housing part 203. The second guide member is located approximately 60 to 130 degrees from the first guide member 206.

FIG. 9 also shows some electronic components that form parts of the blood glucose meter 100. These components are provided within the housing 107 but do not form part of the cartridge 106.

A bus 211 is arranged to connect a number of components including a microprocessor 212, random access memory (RAM) 213, read-only memory (ROM) 214, a keys interface 215, a display driver 216, an analyte interface circuit 219 and a motor interface 217. All of these components are powered by a battery 218, which may take any suitable form.

Stored in the ROM 214 is software and firmware that governs operation of the blood glucose meter 100. The software/firmware is executed by the microprocessor 212 using the RAM 213. The software/firmware stored in the ROM 214 is operable to operate the blood glucose meter 100 such as to allow control by a user through the keys or input devices 101 to 103, as detected by the keys interface 215. A blood glucose measurement and other information is provided on the display 104 at suitable times by operation of the software/firmware and the microprocessor 212 through the display driver 216.

The motor interface 217 allows the microprocessor 212, according to the software/firmware stored in the ROM 214, to control the motor that is coupled to the drive wheel 201, and any other motors that are included in the blood glucose meter 100 (as will be described below).

The analyte interface circuit 219 is operable to provide electrical signals with certain voltages to the electrical contact terminals 401 (described in more detail with respect to FIG. 10), and thus the contact pads 318 and thus the analyte measuring part 316, and to measure parameters of signals such as to allow the microprocessor 212 to measure a blood glucose level of a blood sample.

As previously mentioned, the cartridge may contain a plurality of test disc members 209. These test disc members 209 may be separated from one another by action of a spacer member provided on the underside of each test disc member 209. . The spacer member may comprise a slice of a hollow cylinder centered on the center of the test disc member 209. The inner diameter of the spacer member is selected such that the hole 306 does not overlap with the spacer member. The outer diameter of the spacer member is only slightly greater than the inner diameter, so the spacer member has little thickness. The height of the spacer member is between 0.5 and 1 millimeter. When plural test disc members 209 are stacked together, the spacer member provides separation between the upper surface 303 of one test disc member and the lower surface 304 of the test disc member that is directly above it. The separation is determined by the height of the spacer member. The BGM 100 may be configured to present each test disc member 209 to the aperture 105 in turn as will now be described.

Each of the test disc members 209 commence at the same orientation. A first test disc member 209 is uppermost. The second guide member is located in the notch 301 of the lowermost test disc members. The notch 301 of the first test disc member 209 is aligned with the second guide member, but is not constrained thereby. The upper surface 303 of the uppermost test disc member 209 is in contact with a lowermost surface of the first guide member 206. The test disc members 209 are biased in an upwards direction by bias means (not shown), which may be a spring. However, the test disc members are prevented from moving upwards within the cartridge 106 by virtue of the contact between the upper surface 303 of the first test member 209 and the lowermost end of the first guide member 206.

From the initial position described above, the shaft 204 is caused to rotate in a clockwise direction by action of the drive wheel 201 and drive belt 202. A drive dog (not shown) is engaged with the drive notch 307 in the hole 306 of the test disc member 209, and so allows rotation of the shaft 204 to result in rotation of the test disc member 209. This rotational movement may be configured to cause the removal of the seal 314 covering the lancet housing 300. For example, the inner surface of the cartridge 106 may be provided with a protrusion or gripping mechanism which contacts and removes the seal 314.

Rotation causes the cleaning swab 302 to contact a skin-covered part of a user (hereafter the part will be referred to as a user's digit, for the sake of convenience). The action of this contact and the presence of the alcohol in the cleaning swab 302 cleans and disinfects the part of the user's digit which is to be lanced. Any suitable alcohol could be used, for example a solution of Ethanol or Isopropyl alcohol. This can reduce risk of infection of the wound and also can increase accuracy, in particular by removing any substance from the skin which may interfere with the measurement, for example glucose (as may occur after eating fruit etc.). Alternatively, any suitable antiseptic solution may be used. The antiseptic solution may not contain alcohol.

Further rotation brings the lancet 309 in front of the aperture 105. As such, the user's digit is lanced by the lancet 309. This produces a puncture in the skin of the digit, through which blood can escape. The shaft 204 is caused to rotate only by a predetermined amount, the maximum extent of travel of the lancet 309 is controlled. The penetration of the lancet 309 in the user's digit depends on a number of factors, as will be appreciated by the person skilled in the art. The amount of rotation, and thus the depth of penetration, may be definable by a user. The penetration depth specified by a user may be achieved through software or firmware control of rotation of the shaft 204. The penetration depth may be defined by the user for example using one or more of the first, second and third inputs 101 to 103. For instance, the first and second inputs 101, 102 may be increase and decrease respectively, with the third input 103 being a select or confirm input. The value defining the depth may be stored in memory.

The rotation which performs the cleaning and lancing may be one smooth, continuous rotation. Alternatively, the shaft 204 may be controlled such that the test disc member 209 rotates slowly when the cleaning swab 302 is in contact with the user's digit and thereafter rotates quickly to perform the lancing. A slow rotation while the cleaning swab 302 is in contact with the user's digit may improve the effectiveness of the cleaning. A quick rotation when performing the lancing may reduce the pain involved with the lancing operation.

Subsequently, the shaft 204 is controlled to rotate in an anticlockwise direction. This causes the lancet 309 to be removed from the user's digit. A short time thereafter, the user's digit is again contacted by the cleaning swab 302, although the test disc member 209 is now rotating in the opposite direction to the first contact. This contact removes blood from the site of the lancet puncture. The absorbent material of the cleaning swab 302 aids in this removal. Generally a small volume (or droplet) of blood will have exited the puncture wound. A pause in the rotation of the test disc member 209, after the lancet 309 is removed from the user's digit, may be interposed in order to allow a droplet of blood to form on the surface of the skin. In some blood glucose analysis techniques it is advantageous to exclude this initial droplet from the analysis. The alcohol absorbed within the cleaning swab 302 provides a further disinfecting action as the cleaning swab 302 contacts the puncture wound. In some alternative embodiments, the cleaning swab 302 may only be impregnated with alcohol on its clockwise side (the side furthest from the lancet). An impermeable barrier may be formed within the body of the cleaning swab 302 to ensure that the alcohol solution remains only on one side of the cleaning swab. Alternatively, two separate cleaning swabs 302 may be provided.

If the device is merely a lancing device and is not equipped to perform a blood glucose analysis, use of the device may effectively end at this point. The user removes their digit from the aperture 105 and provides a blood sample to a separate meter. The used test disc member 209 continues to rotate in an anti-clockwise direction until the notch 301 becomes aligned with the first guide member 206.

If the device is a BGM 100, the test disc member 209 continues to rotate until the blood collection part 315 is aligned with the aperture 105. Here, rotation ceases. During this rotation, the user's digit may rub against the edge 305 of the test disc member 209. This may act to increase the pressure on the user's digit and encourage blood to exit the wound. In some embodiments, the edge 305 of the test disc members 209 may be shaped so as to apply a desired amount of pressure and/or to apply pressure periodically. At this location, blood that has been caused to be expelled from the user's digit by the lancet 309 is caused to be drawn to the analyte measuring part 316 by capillary action. The blood and the enzyme then react.

At a suitable time, the shaft 204 is caused to be rotated further in an anticlockwise direction until the notch 301 is aligned with the first guide member 206. At this location, there is nothing preventing upwards movement of the first test disc member 209. As such, all of the test disc members 209 are moved upwards by virtue of the bias means (not shown).

When the first test disc member 209 moves upwards, the drive dog ceases to cooperate with the drive notch 307 of the hole 306 of the first test disc member 209. A lower surface of the drive dog contacts the upper surface 303 of a second test disc member 209 located immediately underneath the first test disc member 209. This prevents further upward movement of the second test disc member 209. At this position, the shaft 204 is caused to be rotated by the drive wheel 201 and the drive belt 202 such that the drive dog is coincident with the drive notch 307 of the second test disc member 209. At this location, the second disc member 209 is able to move upwards on the shaft 204, thereby engaging the drive dog 320 with the drive notch 307 of the second test disc member 209. After the second test disc member 209 has moved upward by a distance equal to the height of the spacer member, further upwards movement of the second test disc member 209 is prevented by contact between the first guide member 206 and the upper surface 303 of the second test disc member 209. At this point the first guide member 206 is located within the notch 301 of the first test disc member 209. This prevents further rotation of the first test disc member 209 within the cartridge 106.

In some embodiments, the upwards movement of the test disc members 209 within the cartridge 106 may cause the removal of the seal 314 covering the lancet housing 300. For example, the inner surface of the cartridge 106 may be provided with a protrusion or gripping mechanism which contacts and removes the seal 314 during this movement. Alternatively, the aperture 105 may have a cover such as a hinged or slidable door. This cover may have protrusions arranged to remove the seal 314 from the lancet housing 300 when the cover is opened. Alternatively, the seal 314 removal mechanism may be a motorised mechanism provided on an inner surface of the cartridge 106 and controlled by the microprocessor 212 to remove the seals 314 while the test disc members 209 are stationary.

After the operation described above the second test disc member 209 is in exactly the same position as was the first test disc member 209 before operation began. Furthermore, the shaft 204, and thus the drive dog, has the same orientation. As such, the second test disc member 209 is able to be used to elicit a blood sample from a user and test the glucose level thereof in the same way as was the first test disc member 209.

By providing a stack of test disc members 209 within the cartridge 106 and by providing a suitable physical arrangement, a cartridge 106 can be used for multiple tests. When the cartridge 106 is new, the test disc members 209 are located in the bottom half of the cartridge 106, with the uppermost test disc member being aligned with the aperture 105. As test disc members are used, the stack of test disc members moves upwards in the cartridge. When the last test disc member is used, the cartridge can be said to be spent. At this stage, all of the test disc members are located in the uppermost portion of the cartridge 106.

It will be appreciated that the number of test disc members 209 that can be accommodated within the cartridge 106, and thus the number of tests that can be provided by a cartridge 106, is a factor of the height of the cartridge 106, and the separation between corresponding parts (e.g. the upper surfaces) of adjacent test disc members 209. A taller cartridge and/or a reduced separation of test disc members increases the number of tests that can be performed using a single cartridge 106.

Figure 10:
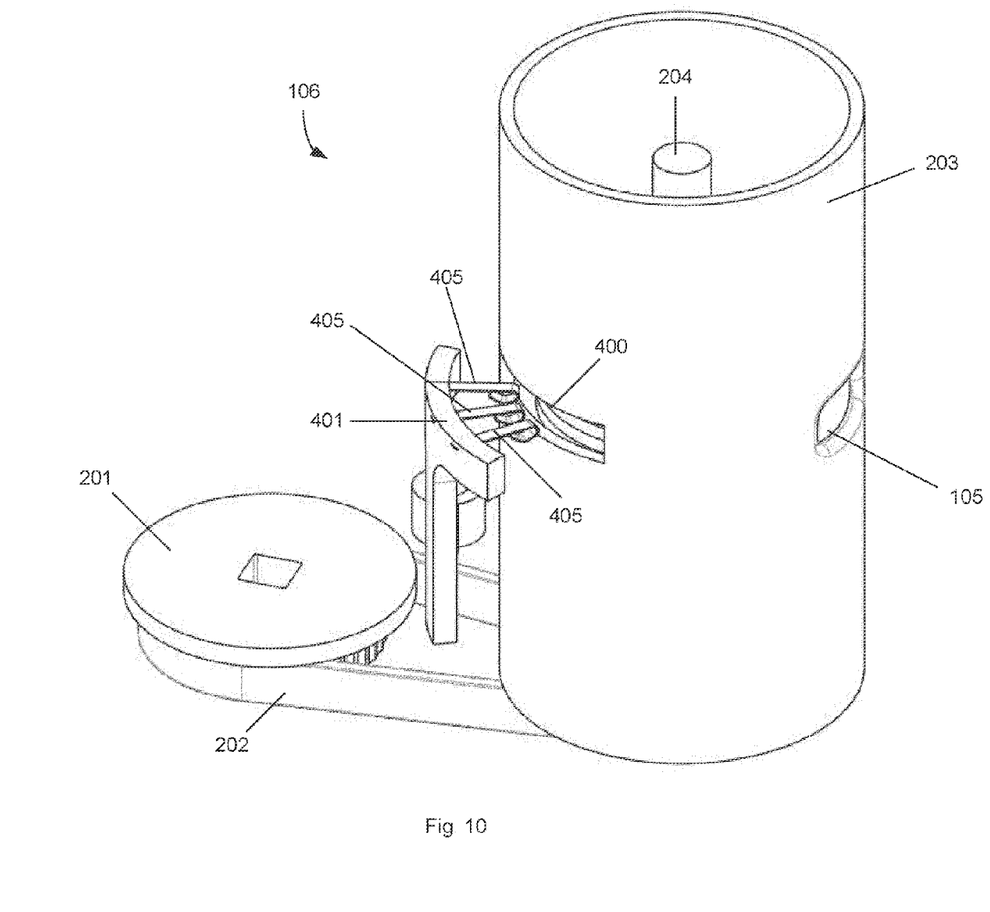
FIG. 10 is a perspective view of components of the BGM of FIG. 5.

Reference will now be made to FIG. 10, which illustrates connection of the analyte measuring part 316 to measurement circuitry (not shown).

The hollow cylindrical housing part 203 is shown with the aperture 105 and the shaft 204 located as described above. A slit aperture 400 is provided in the hollow cylindrical housing part 203. The slit aperture 400 is located at substantially the same height as the aperture 105. However, the slit aperture 400 is located on a side of the hollow cylindrical housing part 203 that is substantially opposite the aperture 105.

The slit aperture 400 does not coincide with the elongate aperture 110 that is formed at the front side of the BGM 100. As such, the slit aperture 400 is not visible when the cartridge 106 is in place within the BGM 100.

Adjacent to the slit aperture 400 is located a swing arm 401. The swing arm 401 is rotatable about a spindle 402. The spindle 402 has an axis that is parallel to the axis of the shaft 204. The axis of the spindle 402 is located above the drive belt 202. A connecting arm (not visible) connects the spindle 402 to the swing arm 401. In this example, the connecting arm is connected to the swing arm 401 by a vertical connector 404. The vertical connector 404 allows the spindle 402 on which the connecting arm is mounted to be located at a different vertical position to the swing arm 401. The spindle 402, the connecting arm and the vertical connector 404 are arranged such that when the connecting arm is rotated on the axis of the spindle 402 the swing arm 401 is moved towards the shaft. The movement of the swing arm 401 is substantially radial with respect to the shaft 204.

Mounted on the swing arm 401 are first to third electrical contact terminals 405. Each includes a generally horizontal arm and a depending contact head. The electrical contact terminals 405 are made of a resilient conductive material, for instance metal. The depending contact heads are angled at their ends furthest from the swing arm 401.

In one position, shown in FIG. 10, the electrical contact terminals 405 are supported by the swing arm 401 such that the dependent contact heads are located within the slit aperture 400 or alternatively outside of the hollow cylindrical housing part 203. When the test disc member 209 is rotated such that the blood collection part 315 is coincident with the aperture 105, the contact pads 318 are coincident/aligned with the slit aperture 400. As the test disc member 209 is held in this position, the connecting arm is caused to rotate around the axis of the spindle 402 such that the swing arm 401 moves towards the shaft 204. The arrangement is such that the depending contact heads of the electrical contact terminals 405, but not the horizontal arms, come into contact with the contact pads 318 as the electrical contact terminals 405 move into the volume above the upper surface 303 of the test disc member 209. The resilient properties of the electrical contact terminals 405 causes the electrical contact terminals to be forced against the contact pads 318. As such, an electrical connection is provided between the horizontal arms of the electrical contact terminals 405 and the analyte measuring part 316. Electronic measuring means (not shown) connected to the electrical contact terminals 405 operate to pass a voltage through the contact terminals 405 and the analyte measuring part 316 and to take measurements of electrical parameters, from which a measurement of an analyte concentration level, for example a blood glucose level, can be determined.

The connecting arm is controlled to remain in this position for a predetermined time or alternatively until it is detected that a blood glucose level measurement has been made, after which the connecting arm is caused to rotate around the shaft 402 so as to remove the electrical contact terminals 405 from the position above the upper surface of the test disc member 209. Once the electrical contact terminals 405 have been retracted, the test disc member 209 is rotated anticlockwise so as to allow the test disc members 209 to move upwards on the shaft 204.

Alternatively or additionally, each of the conductive contacts 318 may be generally concentric with the shaft 402 for at least a part of their length. This can allow the plural terminals 405 to remain in contact with their respective conductive contacts 318 while the member rotates. Thus, for instance, the test disc member 209 could be rotated away from the position in which the blood analysis part is exposed to collect a blood sample whilst allowing the plural terminals 405 to remain in electrical contact with the blood analysis part 316.

It will be appreciated that the maximum permissible height dimension of the electrical contact terminals 405 is determined by the height of the spacer member 308. A thicker spacer member allows larger electrical contact terminals 405 to be used. However, this is at the expense of an increase in separation between adjacent test disc members 209, and thus a reduced capacity for the cartridge 106. The use of electrical contact terminals 405 including a horizontal arm and a depending contact head allows the height dimension of the electrical contact terminals to be minimised whilst allowing good electrical contact between the electrical contact terminals and the contact pads 318 and also allowing the electrical contact terminals 405 to operate correctly over a sufficient number of cycles.

Although in the Figures, the lancet 309 is shown as substantially straight when the seal 314 is removed, in some other embodiments, the lancet 309 may be curved. The lancet 309 may be curved in the direction of lancing such that the lancet 309 is more aligned with the circumference of the test disc member 209 at its distal end than it is at the end that adjoins the disc edge 305. This has the positive effect that when the lancet penetrates a user's digit, or other body part, due to rotation of the test disc member 209, the path taken by the lancet as it penetrates the user's digit more closely matches the shape and orientation of the lancet than is experienced in a corresponding arrangement with a straight lancet.

This effect may be enhanced if the lancet 309 has a cylindrical form and is terminated at the distal end by an oblique cut. In particular, the distal end of the lancet 309 resembles a cylinder that has been cut at an angle that is not perpendicular to the longitudinal axis of the cylinder. As such, the end face of the lancet 309 has the shape of an ellipse. The ellipse has a semi-major axis and a semi-minor axis and the point that is at the end of the semi-major axis that is furthest from the disc edge 305 forms a point. The cut is made through the lancet 309 such that the point is formed extending in a direction that is substantially circumferential with respect to the test disc member 209.

In operation, the lancet 309, cleaning swab 302 and blood collection part 315 remain within the cartridge 106. The aperture 105 is therefore configured such as to allow an amount of the flesh making up the end of the user's digit to be present within the internal volume of the cylindrical part 203 when the user presses the digit up against the aperture 105. When the user applies force into the aperture 105 with the digit, the digit distorts and a bulbous part is provided within the internal diameter of the hollow cylindrical housing part 203. The size of the bulbous part, and in particular the height of the bulbous part, depends on a number of factors, including the physical characteristics of the user's digit and the amount of force that the user applies, as well as the configuration of the aperture 105.

The aperture 105 is dimensioned such that in normal use (i.e. with a typical user applying a typical amount of force) a bulbous part of the user's digit extends into the internal volume of the hollow cylindrical housing part 203 to a depth of approximately 1 millimeter.

Figure 11:
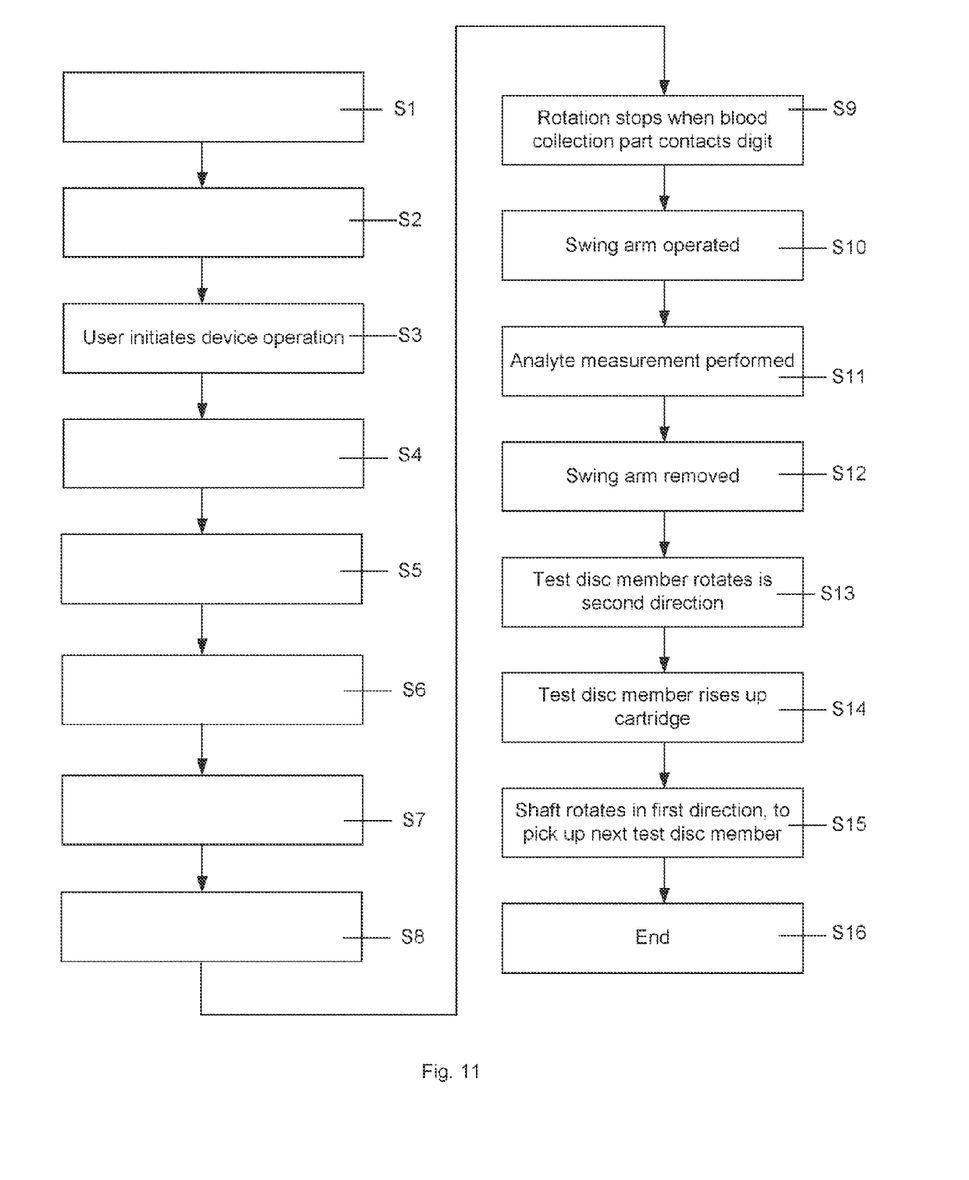
FIG. 11 is a flowchart illustrating operation of embodiments of the lancing devices of FIGS. 1 to 4.

Operation of the blood glucose meter 100 will now be described with reference to the flowchart of FIG. 11. Operation starts at step S1. At step S2, the user locates their digit in the aperture 105. As mentioned above, the user forces their digit into the aperture 105 with a pressure or force that is suitable to allow lancing and blood collection. At step S3, the user initiates device operation. This involves the user pressing one of the inputs 101 to 103. This is detected by the microprocessor 212 by way of the keys interface 215. The software/firmware stored in the ROM 214 uses the key input to call a function or to execute a software module. The software/firmware stored in the ROM 214 then causes the microprocessor 212 to issue a command to a motor attached to the drive wheel 201 through the motor interface 217 to rotate the shaft 204 in a clockwise direction. The test disc member 209 then rotates in a first direction in step S4. The software/firmware controls the extent of the rotation.

At step S5, the cleaning swab 302 contacts the user's digit. The cleaning swab 302 is impregnated with a solution containing alcohol. This cleans and disinfects the user's digit. The cleaning swab 302 is made of an absorbent, compressible material and so deforms when contacting the user's digit.

The test disc member 209 continues to rotate and, at step S6, the amount of rotation is sufficient to lance the user's digit with the lancet 309. The software/firmware stored in the ROM 214 then causes the microprocessor 212 to control the motor to rotate the shaft 204 in the opposite direction, at step S7. As the test disc member rotates anticlockwise, the cleaning swab 302 again contacts the user's digit at step S8. This second contact acts to remove the first droplet of blood which is expressed from the lancet wound. The removal of the blood is enhanced by the absorbent nature of the cleaning swab 302.

Where the device is a lancing apparatus, comprising one or more of the lancing devices 208, involvement of a user in the operation may end after step S8. The user removes their digit from the device in order to provide a blood sample to a separate meter. The process may then jump to step S13, described below Where the device is an all-in-one device for lancing and making a blood glucose measurement, the operation continues at step S9 where the software/firmware causes the microprocessor 212 to control the motor to cease rotation when the shaft 214 is such that the blood collection member 315 is coincident with the aperture 105, and thus the user's digit. At step S10, the software/firmware controls a motor such as to cause the swing arm 401 to be rotated towards the shaft 204. The software/firmware stored in the ROM 214 is such that the microprocessor 212 causes only the required amount of travel of the swing arm 401. At this point, the analyte interface circuit 219 is coupled directly to the blood analyte measuring part 316, which by action of the blood collection part 315 has been provided with blood from the user's digit. At step S11, analyte measurement is performed. This involves the analyte interface circuit 219 providing voltages to the electrical connection contacts 318, and thus to the blood analyte measuring part 316, and measuring parameters of resulting signals. The measured parameters, particularly voltage parameters, are used by the software/firmware stored in the ROM 214, as executed by the processor 212, to calculate a blood glucose measurement level of the user. The blood glucose measurement is then caused by the software/firmware to be displayed on the display 104 through action of the microprocessor 212 on the display drive 216. At step S12, the swing arm is caused to be removed by action of the microprocessor 212, under control of the software stored in the ROM 214, the motor interface 217 and the motor (not shown).

At step S13, the software/firmware results in the microprocessor 212 controlling the drive disc 201 to rotate anticlockwise. Rotation continues until the notch 301 on the test disc member is coincident with the guide 206. At step S14, the test disc member rises up the cartridge 106. In the case where biasing of the test discs up the cartridge 106 is provided by a bias means, for instance a spring, step S14 requires no action on part of the software/firmware and microprocessor 212, although there may be a pause before the next step. In embodiments where movement of the test disc members along the shaft 204 occurs through driving action, step S14 involves the microprocessor 212, under control of the software/firmware stored in the ROM 214, controlling a motor through the motor interface 217. Subsequently, at step S15, the microprocessor 212, under control of the software/firmware stored in the ROM 214, causes the shaft 204 to rotate again in a clockwise direction and to cease rotating when the drive dog engages with the drive slot 307 of the next test disc member in the cartridge 106. At this stage, the test disc members rise up the cartridge 106 slightly.

The operation ends at step S16.

Various modifications and alternative features can be used in connection with the above-described embodiments. Some alternatives now follow.

Embodiments of the invention have been described in which the lancet 309 and the cleaning swab 302 are fixed in relation to one another (excepting that the lancet is flexible and is stored bent towards the cleaning swab). In these embodiments, the lancet 309 and cleaning swab 302 are presented in turn to the digit of a user by rotation of the member on which they are supported. However, the skilled person will appreciate that modifications may be made which allow the lancet 309 and cleaning swab 302 to be moveable relative to one another without going beyond the scope of the invention. For example, a series of lancets 309 and cleaning swabs 302 may be provided on a conveyor system within the cartridge 106. The lancets 309 and cleaning swabs 302 may be moved into position in front of the aperture 105 laterally or axially within the cartridge 106. A single radial actuator may be present within the device and the lancets 309 and cleaning swabs 302 may be positioned in turn in front of the aperture 105 and may be moved in a radial direction towards a user's digit in order to lance and clean respectively.

The analyte measuring part 316 may be sandwiched between two layers of wicking material, the wicking material causing the blood to be drawn through the analyte measuring part 316.

Although in the above the shaft 204 is said to be driven by a drive wheel 201 that is coupled to the shaft 204 by a drive belt 202, the drive may instead be direct (i.e. the drive mechanism is coupled directly to the shaft 204), or connection may be made by a notched belt, a vee belt, or by a direct gear mechanism. Instead of an electric motor, a clockwork drive could be used. A clockwork drive mechanism has a number of advantages, particularly where access to batteries or battery chargers or electricity supplies are limited. In the embodiments in which a clockwork mechanism is used, the user can be sure that the BGM 100 will not cease operating because of drained batteries. A clockwork mechanism may be particularly suited to developing countries and emerging markets.

In embodiments in which an electrical motor is used to drive the shaft 204, preferably control is exerted over the motor by software. In this way, the speed of rotation can easily be controlled. Additionally, the extent of rotation can more easily be controlled. The motor may be a stepper motor.

Alternatively, a mechanical drive arrangement may be present, for instance using a lever or other device for manual actuation. A suitable mechanism may be one similar to those previously used in SLR cameras.

The swing arm 401 may be actuated in any suitable way. For instance, it may be driven by the same motor or mechanism as the shaft 204. Alternatively, it may be driven by a separate motor. In either case, the rotation of the swing arm 401 may be affected by a cam mechanism, or by a pin and slot (track path) mechanism. In the event of an electric motor being used, the motor preferably is software driven. The motor preferably is a stepper motor.

The mechanical arrangement may include a mechanism by which a bias means, for instance a mechanical compression spring, is biased and then released in order to push the electrical contact terminals 405 into place. The terminals 405 can then be refracted by the swing arm 401 using a rotating motion. The overall mechanism can be termed a latch type trigger mechanism.

Instead of a swing arm 401 being used to rotate the electrical contact terminals 405 into place, the contact pads 318 may instead be located on the disc edge 305, allowing the use of fixed electrical contact terminals 405. The electrical contact terminals may include a brush or other deformable feature such that the test disc members 209 can move whilst in contact with the electrical contact terminals without damage occurring to any of the components. Similar arrangements are used in brushed DC motors. In this case the electrical contact terminals 405 could be flexible finger contacts that rest on the periphery of the test disc members 209 in order to contact the contact pads 308.

Alternatively, instead of a swing arm 401, a mechanism may be used to affect longitudinal movement of the electrical contact terminals 405 into place to contact the contact pads 318.

The conductive tracks 317 and the contact pads 318 may be formed by leadframe. Alternatively, overmoulding may be used. Alternatively, printed circuit board (PCB) printing may be used.

Optionally, each of the test disc members 209 is separated from adjacent test disc members by a membrane (not shown in the drawings). In this case, the membrane preferably fits closely to the internal surface of the hollow cylindrical housing part 203. An effect of the membrane is to reduce the possibility of disc cross-contamination. Use of a membrane may allow the test disc members 209 to have a reduced separation than would be the case without the use of a membrane.

In the above, the test disc members 209 are said to be biased upwards by a bias means, for instance a compression spring. Alternative mechanisms for moving the test disc members 209 up the cartridge may be used. For instance, a threaded lifting cam may be provided on the shaft 204 or alternatively on the interior surface of the hollow cylindrical housing part 203. Alternatively, the test disc members 209 may remain stationary, with the aperture 105 and the drive dog instead being moved along the axis of the cartridge 106. Movement of the aperture 105 may be achieved by the use of a sliding door in an elongated slot. Movement of the door allows a different strip to be revealed at the aperture 105.

Instead of the blood collection part 315 wicking blood towards the analyte measuring part 316, blood may be communicated to the analyte measuring part 316 instead through gravity.

In some further embodiments, the BGM 100 may comprise a camera which is embedded or mounted on the housing 107 or cartridge 106. This camera is directed at the aperture 105 and is configured, in conjunction with the microprocessor 212, to detect the presence of blood on the surface of a user's digit. The camera may also, in conjunction with the microprocessor 212, determine the quantity of blood present. The BGM 100 may also have a light source arranged to illuminate the area of lancing in order to allow the camera to make the detection. After lancing the camera and light may be activated and the testing member 209 may remain in a rotational position between the lancet 309 and cleaning swab 302 until it is detected that blood has been expressed from the lancet wound or that at least a predetermined quantity of blood has been expressed. The testing member 209 may then continue to rotate in an anticlockwise direction so that the cleaning swab 302 contacts the user's digit and removes the blood therefrom. The use of the camera in this way may ensure that the first droplet of blood expressed from the wound is removed by the cleaning member 302 and may improve the accuracy of the subsequent measurement by ensuring that a sufficient quantity of the initial (unwanted) blood which is expressed is removed from the measurement procedure.

The invention claimed is:

1. Apparatus for eliciting a blood sample, the apparatus comprising:
    a lancet for lancing a body part of a user; and
    a cleaning member of absorbent material operable to clean a surface of the body part, the apparatus being configured such that in use the lancet is moved to lance a body part of a user and subsequently the cleaning member is moved to contact the body part of the user so as to remove blood from the surface of the body part prior to collection of the blood sample from the surface of the body part.

2. Apparatus according to claim 1, wherein the cleaning member is further configured to contact the body part of the user prior to lancing so as to clean the surface of the body part.

3. Apparatus according to claim 1, wherein the cleaning member contains an antiseptic.

4. Apparatus according to claim 1, wherein the lancet is flexible and resilient.

5. Apparatus according to claim 1, wherein the apparatus is a disc-like member and wherein the lancet and the cleaning member are supported by a housing disposed at an edge of the disc-like member.

6. Apparatus according to claim 1, wherein the apparatus is a testing member and further comprises a blood analysis part for receiving the blood sample.

7. Apparatus according to claim 1, wherein the apparatus is configured to be rotatably mounted on a shaft and to be rotated between a first rotational position and a second rotational position in order to perform the lancing of the body part.

8. Apparatus according to claim 7, wherein the cleaning member is configured to contact the user's body part to remove blood from the surface thereof during rotation between the second rotational position and the first rotational position.

9. Apparatus according to claim 1, the apparatus further comprising:
   a camera configured to capture images of the user's body part; and
   a processor configured to:
      control operation of the camera;
      receive the captured images; and
      determine whether blood is present on the surface of the user's body part.

10. Apparatus according to claim 1, the apparatus further comprising a seal arranged to cover the lancet and the cleaning member.

11. Apparatus according to claim 10, wherein the whole of the lancet is arranged to be retained within a boundary defined by the seal in a first configuration and wherein a cutting end of the lancet is arranged to protrude beyond a boundary defined by the seal in a second configuration.

12. A device comprising:
    a housing;
    a shaft supported within the housing; and
    a plurality of apparatuses each according to claim 1, wherein each apparatus is rotatably mounted on the shaft and is moveable along the shaft.

13. A device according to claim 12 further comprising a seal arranged to cover the lancet and the cleaning member, wherein the seal of each apparatus is configured to be removed by rotational movement of that apparatus within the housing.

14. A device according to claim 13 further comprising a seal arranged to cover the lancet and the cleaning member, wherein the seal of each apparatus is configured to be removed by movement of that apparatus along the shaft.

15. A method of operating a lancing device comprising means for receiving a body part of a user and a rotatable testing member having a lancet and a cleaning member, the method comprising;
    rotating the testing member in a first direction such that the cleaning member contacts a body part of a user received in the receiving means;
    rotating the testing member further in the first direction such that the body part of the user is lanced by the lancet; and
    rotating the testing member in a second direction such that the cleaning member contacts the body part of the user so as to remove blood from the surface of the body part.

* * * * *